United States Patent [19]

Robson

[11] Patent Number: 5,233,986
[45] Date of Patent: Aug. 10, 1993

[54] TIME DOMAIN REFLECTOMETER-INTEGRITY TESTING SYSTEM AND METHOD FOR MEDICAL DEVICE ELECTRODE

[75] Inventor: Jack R. Robson, Beech Grove, Ind.

[73] Assignee: Random Technologies, Inc., Indianapolis, Ind.

[21] Appl. No.: 971,415

[22] Filed: Nov. 4, 1992

Related U.S. Application Data

[63] Continuation-in-part of Ser. No. 866,850, Apr. 10, 1992.

[51] Int. Cl.⁵ .............................................. A61N 1/362
[52] U.S. Cl. .......................................... 607/4; 607/27; 607/29
[58] Field of Search ................................... 128/419.046

[56] References Cited

U.S. PATENT DOCUMENTS

| | | | |
|---|---|---|---|
| 3,922,914 | 12/1975 | Fuchs | 73/290 R |
| 4,466,288 | 8/1984 | Grynberg et al. | 73/654 |
| 4,786,857 | 11/1988 | Mohr et al. | 324/58.5 BO |
| 4,843,234 | 7/1989 | Berthold et al. | 250/227 |
| 4,893,895 | 1/1990 | Berthold et al. | 350/96 |
| 4,960,989 | 10/1990 | Liebenrood et al. | 250/227 |
| 5,033,826 | 7/1991 | Kozner | 350/355 |

OTHER PUBLICATIONS

Tektronix 1520C Metallic Time Domain Reflectometer Service Manual Tektronix, Inc., Jul. 1991 pp. 5-1 to 5-11.
Quantum ®II-Intermedics ® Cardiac Pulse Generator Physician's Manual Models 253-25 and 254-30, Jan. 1990.
Pacesetter ® Technical Manual-APSII Model 3000 Programmed with Model 3030 Function Pak, 1988.
Cordis Corporation 1986 "What Do These Pacers Have in Common?"
Tektronix 1520C Metallic Time Domain Reflectometer Operator Manual May 1990.
Genesis TM Cardiac Pacing System Model 285 Technical Manual, Pacesetter Systems, Inc. 1985 #9190420-001.
Ventak ® PAICD TM Model 1600 Physician's Manual Automatic Implantables Cardioverter-Deflator 1991.
Hewlett-Packard Application Note 1962 "TDR Fundamentals" Apr. 1988.
Hewlett-Packard Application Note 62-1 "Improving Time Domain Network Analysis Measurements" Apr. 1988.
Hewlett-Packard Application Note 62-3 "Advanced TDR Techniques"May 1990.

Primary Examiner—William E. Kamm
Attorney, Agent, or Firm—Baker & Daniels

[57] ABSTRACT

A device and method for testing the integrity of an electrode/wire, such as a pacemaker electrode, and electrical wires connected thereto has a receptacle for an electrode and includes a time domain reflectometer comprising an output signal mechanism operatively connected to the electrode receptacle. The method of analyzing the integrity of an electrode comprises the steps of generating a time domain reflectometer (TDR) reading (output signal) from the electrode, and transmitting the signal to an output device. The output signal may be analyzed to determined whether it varies by a predetermined threshold, or it may be displayed so that differences in the electrical characteristics of the electrode may be identified. The present invention allows a cardiologist or technician to ensure that the electrode is properly engaged and to determine the integrity of the electrode.

23 Claims, 8 Drawing Sheets

| NO. | READING DATE | COMMENTS | PHYSICIAN |
|---|---|---|---|
| 1/512 | 01/01/92 | PRE-IMPLANT READINGS W/ TECHTRONICS 1000 | SMITH, J. |
| 2/512 | 01/01/92 | IMPLANTED W/ TECHTRONICS 1000 ELECTRODE | SMITH, J. |
| 3/512 | 02/01/92 | POST-OPERATIVE CHECK-UP | SMITH, J. |
| 4/512 | 07/01/92 | 6 MONTH CHECK-UP OK | JONES, D. |
| 5/512 | 09/15/92 | PATIENT COMPLAINTS OF FATIGUE - CHECKS OK | SMITH, J. |

PRESS ▲ ▼ TO HIGHLIGHT, SELECT TO SELECT

FIG. 3

| ELECTRODE MANUFACTURER | MODEL NO. |
|---|---|
| CARDIAC PACEMAKERS, INC. | CPI 1000 |
| CARDIAC PACEMAKERS, INC. | CPI 1100 |
| INTERMEDICS, INC. | 254-001 |
| INTERMEDICS, INC. | ELECPRO 100 |
| PACESETTER SYSTEMS, INC. | PACE-3000 |

PRESS ▲ ▼ TO HIGHLIGHT, SELECT TO SELECT

TIME DOMAIN REFLECTOMETER-INTEGRITY TESTING SYSTEM AND METHOD FOR MEDICAL DEVICE ELECTRODE

CROSS REFERENCE TO RELATED APPLICATIONS

This is a continuation-in-part of application Ser. No. 07/866,850 filed Apr. 10, 1992.

FIELD OF THE INVENTION

This invention relates to a device, system and method used in medical testing, and, in particular, to a technique for testing the integrity of an electrode or cable (or combination thereof) through which electrical signals, such a heart pacing pulses, pass.

BACKGROUND OF THE INVENTION

A number of medical devices are available which provide assistance in the performance of various physiological functions for an individual experiencing difficulties. Some of these devices are implanted within the patient's body while others are external and are typically utilized under temporary or emergency situations. Whether residing inside or outside of the patient's body, many devices include an electrode or cable connected to the patient for the performance of a physiological function or for the receipt of information from the patient. Cardiac pacemakers, defibrillators, the Jarvis heart and insulin pumps are a few examples of devices which may be implanted within the patient's body. External devices also include cardiac pacemakers and defibrillators and ECG monitors and other diagnostic equipment.

External pacemakers, defibrillators and the like are usually portable devices which are battery-powered and capable of being recharged. The device's portability is important because it is typically used in emergency situations or as a temporary resolution to a patient's problems before a more permanent solution can be rendered. For example, defibrillators may be carried in an ambulance or used in hospital emergency rooms to revive a patient or to restore a normal heart rhythm. An external pacemaker may be used to provide assistance to a patient who has not yet had an internal pacemaker implanted or to provide pacing while the patient is in surgery to implant or replace an implantable pacemaker.

To provide signals to the medical electrodes, or to receive signals from the patient as is necessary for monitoring, diagnostic or other functions of the device, cables, electrodes or wires extend from the device to the patient. For example, the Medtronic Model 5345 Temporary Pulse Generator, available from Medtronic, Inc. of Minneapolis, Minn., is a temporary pacemaker such as may be used by a patient prior to implanting a permanent pacemaker. A patient cable is connected to the device and unipolar or bipolar pacing leads contacting the patient are connected to the patient cable. The Medtronic model 5311 pacing system analyzer is used to test sensing and pacing thresholds of heart electrodes. The Code Master Defibrillators, available from Hewlett Packard of Andover, Mass., provide the capabilities of defibrillation and ECG monitoring. Both integral defibrillator paddles and optional gel electrodes may be used with the device to accomplish these functions. Similarly the Lifepak ® 6 Cardiac Care System, available from Physio-Control ® Corporation of Redmond, Wash., uses paddles for defibrillation and patient cables for monitoring ECG. A combination pacemaker and defibrillator such as the Zoll PD TM 1200 Pacemaker/Defibrillator, available from ZMI Corporation of Woburn, Mass., uses paddles or gel electrodes for defibrillation and gel electrodes for pacing and for monitoring ECG signals. In all instances, the integrity of the defibrillator, patient cable, or electrode is of utmost importance for the proper operation of the external device.

Presently, most portable pacemakers and defibrillators are periodically checked by hospital staff to determine only whether the most basic functionality exists. For example, a nurse may check such a unit to determine whether it is plugged in, whether the proper display appears when the unit is switched on, and whether an appropriate quantity of ancillary supplies, such as pacing pads, are readily available. However, other aspects of the system do not lend themselves to being readily checked. For example, many connectors between the cables, leads, electrodes or pads of such systems may become loose or bent, resulting in a poor or open circuit. For such systems, there may be no apparent indication that the equipment is faulty, causing the defective equipment to be used on patients in critical condition. The only way to detect such an equipment failure is for an astute medical technician to notice that all of the patients on which the defective equipment had been recently used had died, and to have the equipment thoroughly inspected by an advanced medical technician.

Some external devices, such as the Code Master Defibrillators and the Zoll PD TM 1200 Pacemaker/Defibrillator, provide information to the operator or technician regarding the "integrity" of the electrode. Specifically, these systems provide a warning when a complete circuit is not provided. A complete circuit is one in which there is current flow between the electrodes and there are no severe discontinuities in the electrodes. Thus, the electrodes must be place against a patient's body to complete an electrical circuit in order to determine whether a break exists in the cables, electrodes or the connectors of either. Because the cables or electrodes must contact the patient before a test may be performed does not allow a fault in the system to be identified until the system must be used. Furthermore, because time is of the essence when the device is utilized on a patient, it is desirable to provide an integrity testing system for the electrodes or cables connected to such external devices which does not require that the patient be connected to the electrodes or cables so that the cables or electrodes may be tested on a routine basis. In addition, it is desirable to provide a system that not only indicates whether there is an open circuit in a medical electrical system, but location of the open circuit, e.g. whether the break occurs where the cables plug into the pulse generating unit, the connector between the cables and the pacing pads, or in the middle of the wires of any of the cables.

Many of the electrodes used with these external devices are disposable. A sterilized package containing the electrodes is opened just prior to use. Thus, it is also desirable to provide an electrode integrity testing system which is time efficient so as to avoid delaying the provision of the assistance necessary. Furthermore, because physicians will often be utilizing an integrity testing system under stressful circumstances, it must be easy to use and the results of the test must lead to quick interpretation of the integrity of the electrodes or cables.

It is also possible for a problem to occur with the integrity of the cables or electrodes during their use. For example, leads may become disconnected from the patient or from the device or the cable to which the lead is connected. Therefore, it is desirable to provide an integrity testing system which can be operated during the device's operation and which does not interfere with the device's other functions.

Time domain reflectometers, such as the 1502C Metallic Time Domain Reflectometer manufactured by Tektronix, Inc. of Beaverton, Oreg., are used to test the integrity of cable such as co-axial cables. For such integrity testing, time domain reflectometers send electrical pulses down the cable and detect any reflections may by any discontinuities in the cable. Specifically, time domain reflectometers send out successive pulses and measure the respective reflected pulses at times corresponding to points along the cable. Measurements are provided in terms of voltage versus time which can then be converted to resistance over the length of the cable. Time domain reflectometers can locate shorts, opens, defects in the shield of the cable, foreign substances in the cable, kinks, and more. Generally, only one parameter is required for the proper operation of the time domain reflectometer in determining the integrity of a cable. That parameter is the velocity of propagation or the speed of the signal down the cable which varies for different cable dielectric materials. Time domain reflectometers may operate on either a closed or an open circuit. For an open circuit the signal continues to be reflected from the wire and returns to the instrument. In general, variations in the resistance measured by the time domain reflectometer indicates a fault such as a bad connection, the stripping of insulation, pressure on the cable, or a break in the cable.

Time domain reflectometry has been used for a variety of applications. In U.S. Pat. No. 4,466,288, time domain reflectometry is used to evaluate vibrations. The level of fluid in a vessel may be determined by time domain reflectometry as disclosed in U.S. Pat. No. 3,922,914. Also, the constituents of a multi-phased fluid system have been evaluated as disclosed in U.S. Pat. No. 4,786,857.

In addition, time domain reflectometry has been used for optical systems as well. For example, optical time domain reflectometers, such as that disclosed in U.S. Pat. No. 4,960,989, may be used to determine the tip location of a consumable electrode within an electric furnace as disclosed in U.S. Pat. No. 4,843,234. Similarly, optical time domain reflectometry is used in U.S. Pat. No. 5,033,826 to determine which surface of a photographic lens is impairing transmissivity.

U.S. patent application Ser. No. 07/866,850, filed Apr. 10, 1992, discloses an integrity testing system for implantable electrodes such as may be utilized with implanted pacemakers or defibrillators. The electrical device disclosed in U.S. patent application Ser. No. 07/866,850 has a receptacle for an electrode and includes a time domain reflectometer comprising an output signal mechanism operatively connected to the electrode receptacle. The method of analyzing the integrity of an implanted electrode comprises the steps of generating a time domain reflectometer (TDR) reading (output signal) from the electrode, and transmitting the signal to an output device. The output signal may be analyzed to determine whether it varies by a predetermined threshold, or it may be compared to a previously generated signal from the electrode so that differences in the electrical characteristics of the electrode may be identified. The invention allows a cardiologist or technician to ensure that the electrode is properly implanted and to non-invasively determine the integrity of the electrode over a patient's life.

It is desirable to provide a method and device using time domain reflectometry to determine the integrity of electrodes or cables connected to an external device to thereby alert the cardiologist or the technician of a potential or existing problem associated with the electrode or cable. As indicated above, time domain reflectometry may be used with both unipolar or bipolar electrodes. The velocity of propagation of any electrode is necessary for time domain reflectometry measurements. Such a parameter could be stored in the device.

It is also desirable to provide a method of analyzing the integrity of the electrode or cable connected to the external device. Such analysis could be completed in within the device. Of course, to be used in conjunction with the portable devices, the integrity testing system must be able to be integrated within the device and must not consume a great deal of power.

OBJECTS OF THE INVENTION

Accordingly, it is one object of the present invention is to provide a method and apparatus for testing the integrity of cables, leads and/or electrodes connected to external medical devices, such as defibrillators, temporary pacemakers or pacing system analyzers, to thereby alert the physician or a technician of potential for existing problems associated with the electrode or cable that may be detrimental to the patient.

It is another object of the present invention to provide a method for testing the integrity of such cables and/or electrodes which does not require that the electrode be in contact with a patient during such testing and therefore may be performed on a routine basis.

It is yet another object of the present invention to provide a testing system which is easy to use and time efficient to avoid any delay in the operation of the medical device's normal functions.

It is still another object of the present invention to provide an integrity testing system which does interfere with the normal operation of the medical device, may be integrated into the medical device and does not consume a great deal of power to operate.

SUMMARY OF THE INVENTION

The invention comprises a device and method for testing the integrity of an electrode. The electrical device has a receptacle for an electrode and includes a time domain reflectometer comprising an output signal mechanism operatively connected to the electrode receptacle. The method of analyzing the integrity of an electrode comprises the steps of generating a time domain reflectometer (TDR) reading (output signal) from the electrode, and transmitting the signal to an output device. The output signal may be analyzed to determined whether it varies by a predetermined threshold, or it may be displayed so that differences in the electrical characteristics of the electrode may be identified. The present invention allows a cardiologist or technician to ensure that the electrode is properly engaged and to determine the integrity of the electrode.

DETAILED DESCRIPTION

Figure 1:
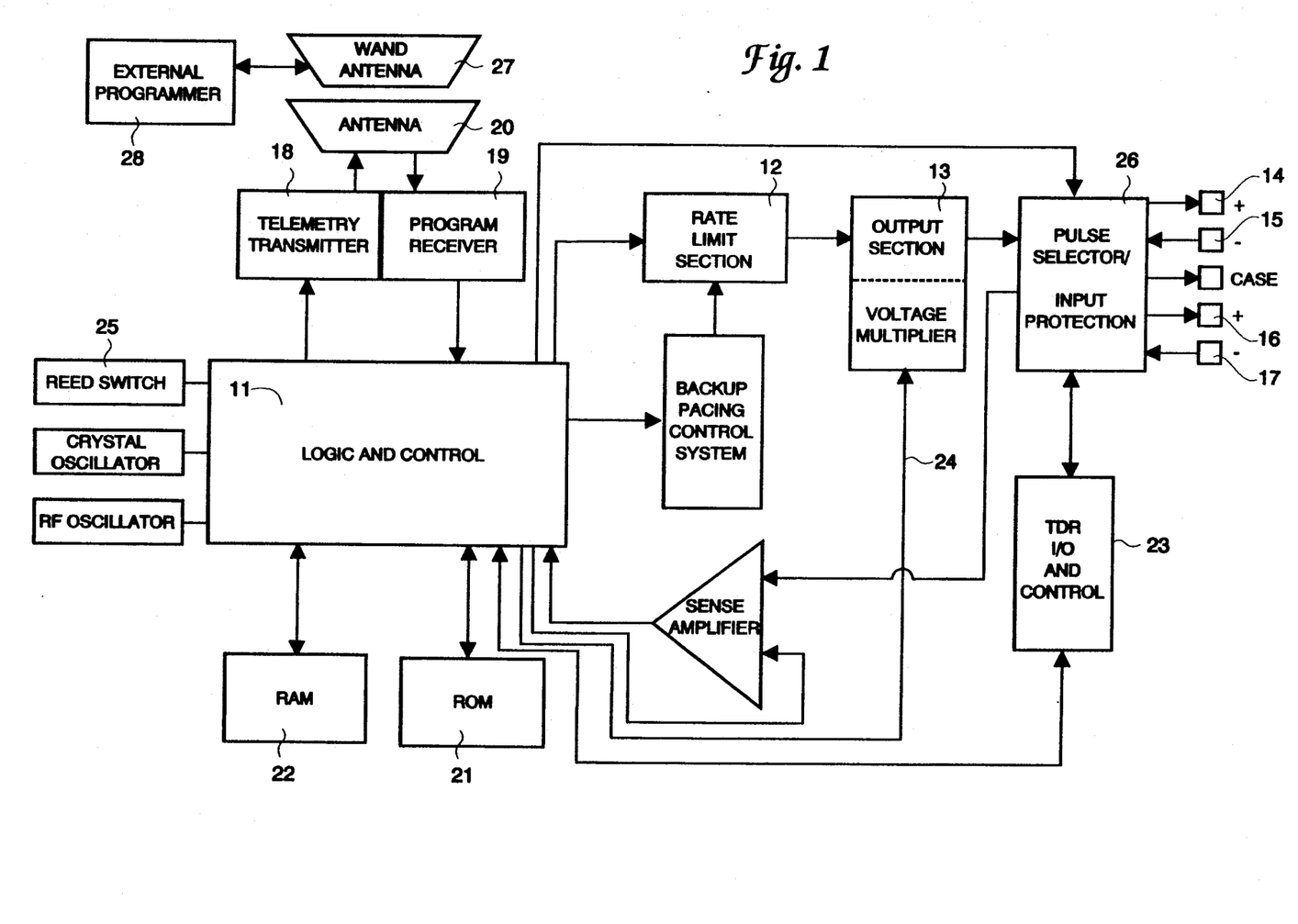
FIG. 1 shows a block diagram of one embodiment of a device of the present invention when used in connection with a programmable cardiac pacemaker.

Referring to FIG. 1, there is shown a representative block diagram of one embodiment of the present invention. In this embodiment, the invention is located in an implantable multi-programmable pacemaker, which includes logic and control unit 11 (which includes a CPU and appropriate software to carry out the functions described herein), rate limit section 12, and output section/voltage multiplier 13. Conventional microcircuitry, and preferably, an application specific integrated circuit, is used to package the TDR and other components in the implantable case. The pacemaker is designed to provide periodic pulse to two implantable pacing electrodes through electrode receiving means, namely connectors 14 and 15, and 16 and 17 respectively. However, the invention may also be used with a device connected to a single electrode. Connected to logic and control unit 11 is a telemetry system comprised of telemetry transmitter 18 and program receiver 19, both of which on connected to common antenna 20. The telemetry system allows the pacemaker to be interrogated to determine its operating conditions after it has been implanted, and also allows the pacemaker to be reprogrammed without surgery. For example, the device can be reprogrammed to generate stimulating pulses on the pacing electrode at set rate, or at a varying rate depending on cardiac activity. Other parameters, such as the pulse width and pulse amplitude can also be specified after the pacemaker has been implanted. These operating parameters are stored in random access memory (RAM) 22, while the control program is stored in read only memory (ROM) 21. Reprogramming is accomplished through the use of an external system programmer 28 having an RF transceiver wand 27, although a convention serial data port with lead connectors extending through the skin of the patient may also be used.

The invention also includes time domain reflectometer (TDR) I/O control 23, which includes the circuitry necessary to generate a TDR pulse on the electrodes and to detect the resulting voltage. A TDR applies a narrow pulse of current (typically by a tunnel diode) to the electrode and monitors the resulting reflected voltage on the electrode over a period of time. A stored reflected voltage waveform comprises a raw TDR reading. If the electrode has a known propagation velocity ($V_p$), the time delay to a particular reflection may be interpreted in distance from the pulse generator. This would include the pacemaker's internal wiring to the pacing electrode connectors, the electrical connection between the connectors and the pacing electrode, and the entire length of the pacing electrode, terminating in the portion placed in heart tissue. The amplitude of the reflected voltage is a function of the electrode impedance and the applied pulse, and therefore can be interpreted in dB, or in rho, which is a function of impedance. Circuitry for time domain reflectometers is well-known and, in isolation, do not form the present invention. In general, a TDR comprises an I/O controller, a digital timebase, an analog timebase, and a pulse generator. As described further below and shown in FIG. 8, the TDR generates a short, square output pulse. After a predetermined amount of time has passed (the TDR base time), the pulse as reflected back by the electrode is monitored. This comprises means for deferring the storing of the TDR signal until the amount time specified by the TDR base time signal has elapsed after the generation of a TDR incident pulse. At a specific time, as determined by the digital timebase, a portion or "slice" of the reflected wave is stored in an analog timebase. This value is then converted to a digital value by an analog to digital converter and stored in memory. The pulse generating-wave storing process is repeated, except that the time period between the pulse generation an when a portion of the reflected wave is stored is increased slightly, causing a different "slice" of the reflected wave to be stored. After a sufficient number of samples (e.g., 256) have been collected, a compilation of the stored waveform reading (a "TDR reading") provides a view of the entire reflected wave. A representative TDR pulse may comprise a 300 mV amplitude into a 50 ohm load, with a 25 microsecond pulse duration, and the reflected rise may be detected in less than 200 picoseconds. To test for an open circuit, the system may merely measure the time between the incident pulse and the beginning of the reflected waveform.

In general, the present invention operates in the following manner. Logic and control 11 is designed to periodically send pacing signals via output line 24 to output section/voltage multiplier 13. Logic and control section 11 is programmed to cause output section/voltage multiplier to generate cardiac stimulating pulses of predetermined amplitude, duration and frequency according to parameters stored in RAM 22. A typical cardiac pacemaker generates stimulating pulses at frequencies of 0.5 to 3 per second, at amplitudes from 2.5

V to 8.5 V, and at durations of 0.15 to 2.3 milliseconds. Accordingly there is a substantial time gap of at least 300 milliseconds between pulses. As a complete TDR pulse and reflection reading time can be accomplished with a pulse repetition rate of 200 microseconds, it is possible to take an entire set of 256 readings in well under 60 milliseconds. Thus a complete TDR reading can be generated between the stimulating pulses periodically provided to the pacing electrode. However, it is also within the scope of the invention to space out the TDR pulses between multiple stimulating pulses.

Prior to implantation of the device in body, the device will be programmed with various default parameters. Conventional pacemakers are programmed, for example to specify the stimulating pulse repetition rate, pulse amplitude, positive and negative sensitivities and control mode. Prior to implantation, one or more pacing electrodes will be selected and connected to pacing leads 14, 15 and 16, 17 of the pacemaker. Each model of electrode has its own characteristics, including a textual model number, polarity, number of filaments, electrical length, physical length, $V_p$ and source resistance. Representative electrode parameters to assist in taking later TDR readings, are shown as electrode menu options 40 in FIG. 2. In addition, each electrode will ideally have a set of default sampling 41 and display 42 options. Preferably, the electrode parameters, sampling and display options may be specified by the electrode manufacturer and used to set default values in the pacemaker prior to implantation. Storing these parameters into the pacemaker is accomplished using conventional telemetry programming equipment with appropriate software to carry out the functions described herein.

To program the default electrode, sampling and display options into the pacemaker, external programmer 28 is first turned on, and the telemetry head of wand antenna 27 is positioned over the pacemaker. The telemetry head generates a magnetic field which activates reed switch 25 inside the pacemaker. This switch causes logic and control unit 11 to activate program receiver 19 and to receive instructions from programmer 28. In one embodiment of the invention, programmer 28 has a touch screen and various options are selected by touching the indicated portion of the screen. The physician will initially step through the prompts displayed on programmer 28 to transmit the desired pacemaker settings (e.g. stimulation rate, pulse amplitudes, sensitivities and mode) into the pacemaker. The physician may then select a TDR option on programmer 28, which will cause programmer 28 permit the TDR parameters to be specified and displayed, such as through the TDR options screen shown in FIG. 2.

Figure 4:
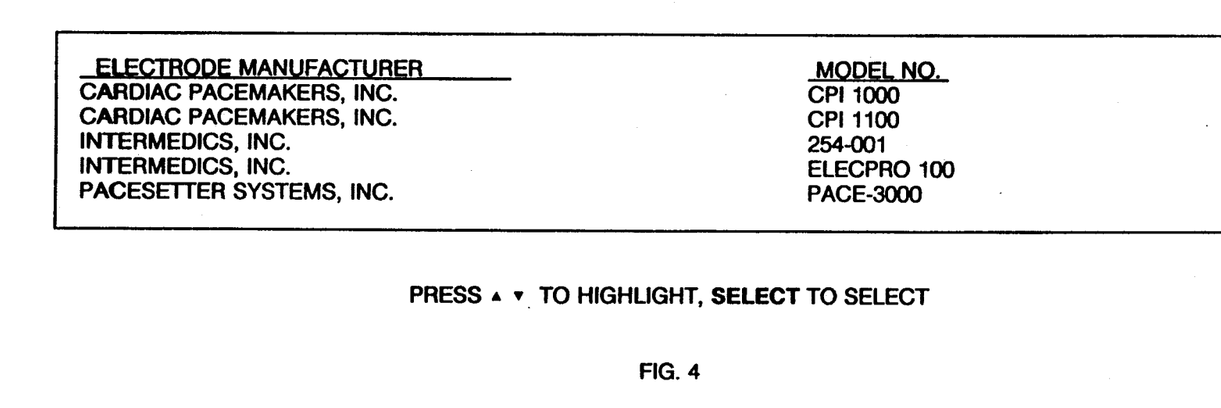
FIG. 4 is a representative computer screen list window displaying a partial index of electrode manufacturers and models, one of which may be selected to provide a set of default electrode, sampling and display options for a particular electrode.

The physician will initially wish to specify the default TDR values to be stored in the pacemaker. Ideally, programmer 28 will include a database of electrode manufacturers and models, with default electrode, sampling and display options for each electrode model. The database may be periodically updated by programmer 28 manufacturer via a floppy disk with information concerning new electrodes on the market. When the physician first enters the TDR menu, the top "Read Configuration for Pacemaker" option will be highlighted in reverse video. To select a default electrode configuration from the database, the physician presses down arrow 43 to cause the "Select Configuration from Electrode Database" option to be highlighted. The physician then depresses the Select button 50 on the screen. This causes an overlapping window to be displayed on the screen as shown in FIG. 4, displaying a list of electrode manufacturers and model numbers. The physician may repeatedly depress the down arrow until the electrode to be implanted is highlighted, then depress the Select option 50 on the touch screen. This will close the display window, and cause the Electrode, Sampling and Display options to be set to the default values recorded in the database for the particular electrode. While in this window (or any other window which may be opened) at any time prior to depressing the Select option 50, the physician may depress the Escape 47 portion on the screen, which will close the window and cause the display to revert to its previous status. A representative window and set of electrode default information values is shown in FIG. 1. Should the physician desire to change any of the default values, the physician may repeatedly depress the down arrow until the value to be changed is highlighted. The physician may then depress the left 48 and/or right 49 arrows, which will cause the highlighted values to be decremented or incremented, respectively.

After the physician has specified the desired electrode configuration values, the physician may store them in the pacemaker so that they do not have to be reprogrammed each time a TDR reading is taken. This is done by depressing the up or down arrows until the "Store Configuration to Pacemaker" option is selected. The Select button is then depressed, which causes all of the displayed electrode information to be transmitted to the pacemaker by RF transceiver 27 and stored in RAM 22. If the pacemaker provides means for connecting to a second electrode, such as for multiple leads, or includes two leads for single electrode (i.e. a pulse and a ground) then the pacemaker RAM 22 may be configured with sufficient memory to store a separate setting for each electrode or lead. In addition, pulse selector will include switch means for selecting whether the time domain reflectometer is operably connected to the means for connecting the first implantable electrode or the means for connecting to the second implantable electrode. The location for each storage will be designated by the "Electrode No." option in FIG. 2. If a pacemaker having capability for storing only one set of electrode readings receives an instruction and data to store electrode settings for an electrode other than no. 1, the number information may be ignored and the values replaced by the received values.

After this information has been specified, and prior to implantation, the physician may take an initial TDR reading. This is done by using the up and down arrows to highlight the "Obtain TDR Reading" option, the depressing the Select option 50 on the touch screen. This action causes programmer 28 to transmit a command to the pacemaker commanding the pacemaker to take a TDR reading according to the parameters stored in RAM 22.

Figure 8:
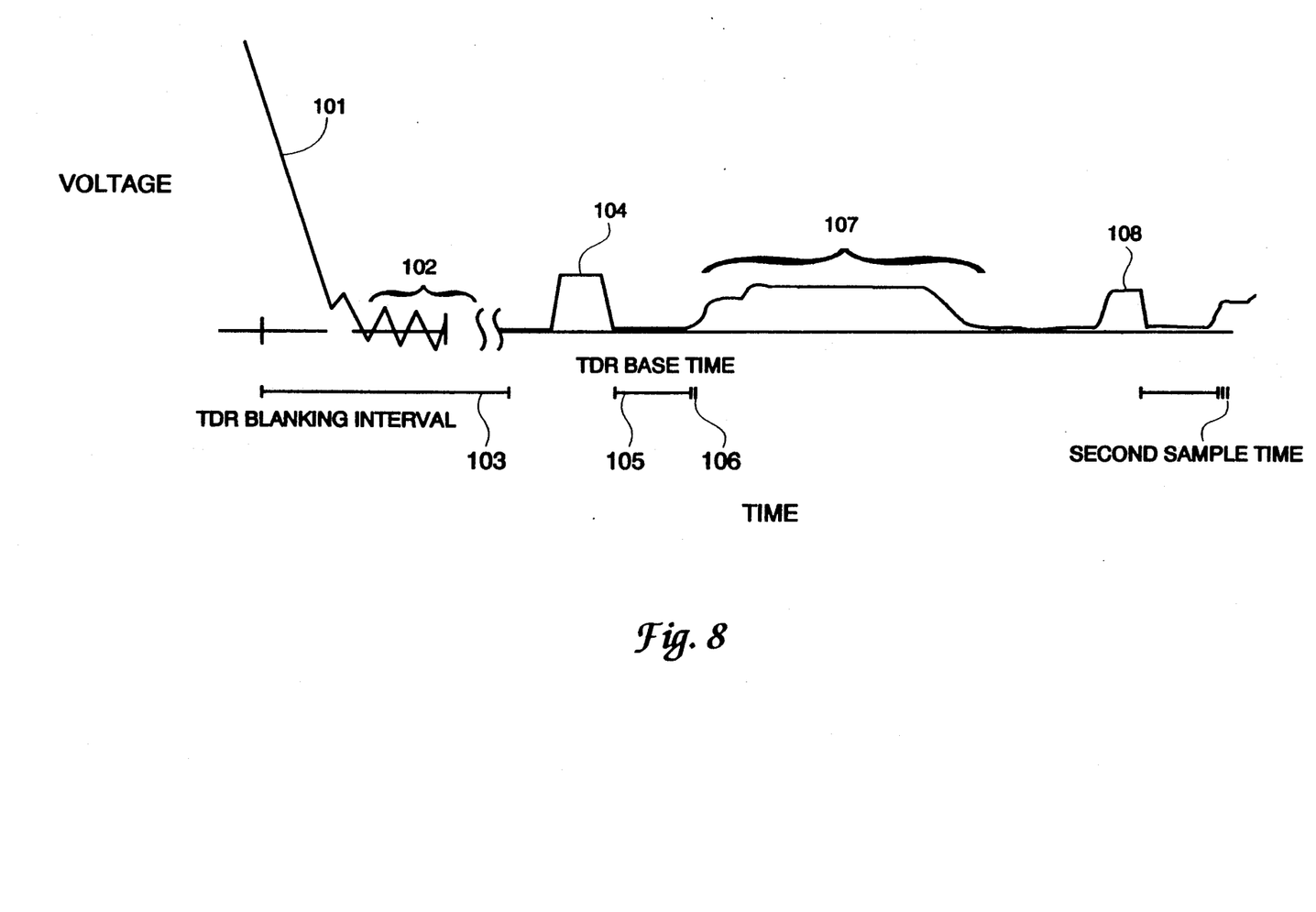
FIG. 8 is a representative time graph showing the trailing end of a stimulating pulse on the electrode, a TDR incident pulse, and reflective pulse.

When the pacemaker receives an instruction to take a TDR reading, the pacemaker waits until no stimulating pulse is present on the electrode. Referring to FIG. 8, normally, if stimulating pulses are being generated on a periodic basis, logic and control unit 11 will wait until the trailing edge of stimulating pulse 101 has been generated. Because stimulating pulse 101 may cause noise to be present on the electrode for a short time period after the pulse is generated, no action is taken during the time previously specified as TDR Blanking Interval 103. This system comprises means for deferring generation of the TDR incident pulse until the amount of time specified by the TDR blanking interval has elapsed after the transmission of a stimulating pulse on the electrode, or the detection of an identified physiological event. For stimulating pulse electrodes, this allows voltage on the electrode to completely drain until the TDR reading process begins. Also, some sensing electrodes, such as those used to monitor heart activity, may have a rhythmic voltage on them generated by an internal organ. Such electrodes are used, for example, to monitor cardiac activity, and logic and control unite 11 section of the pacemaker is capable of determining, at any point in time, the status of the rhythmic activity. For such electrodes, it is desirable to time each TDR reading to begin at the same time in the rhythmic cycle so that each TDR reading is taken at the same time of the rhythmic cycle, and therefore less subject to noise. For a cardiac sensing electrode, TDR blanking interval 103 may begin after completing of physiological event such as the atrial beat, as sensed by logic and control 11, and last for 300 milliseconds. After the 300 millisecond blanking interval, the TDR reading (or readings) may be made, as further described below, and the readings may be completed before the ventricular beat begins. This method, in combination of the minimal current needed to generate a TDR incident pulse, minimizes the likelihood of causing an irregular heartbeat. This system constitutes an anti-coincidence detector adapted to prevent a stimulating signal or physiological event from interfering with the incident pulse signal generated by the time domain reflectometer and its reflected wave.

After the TDR blanking interval has passed, logic and control system 11 sends an signal to pulse selector unit 26, which causes the electrode leads to be switched from an electrical connection with output section 13 to the TDR I/O and control section 23. (During normal pacemaker operation, TDR I/O and control 23 is insulated by pulse selector 26 from the stimulating pulses, to minimize the possibility that the relatively large currents and voltages of the stimulating pulses will harm the TDR circuitry.) Logic and control 11 then sends a signal to TDR I/O and control 23, which comprises means for transmitting an electrical signal to the electrode receiving means, commanding the TDR to generate an incident pulse 104 (see FIG. 8) on the selected electrode lead.

In one embodiment of the invention, logic and control section 11 may include in the signal it sends to TDR I/O 23 a signal representing a impedance through which the TDR pulse should be sent. Ideally, the impedance equals the impedance of the electrode. Accordingly, TDR I/O 23 may include an internal array of source resistors of various impedances through which an incident pulse may be transmitted, and be connected to a multiplexor to select which resistor the pulse should be transmitted. This provides a preferred TDR reflection waveform.

After generation of incident pulse 104, TDR I/O waits the amount of time represented by TDR Base time 105. Normally, this amount of time will be selected to represent the amount of time it will take for a reflected pulse to be detected by TDR I/O 23, and may be on the order of 1-10,000 nanoseconds, depending on the electrical characteristics and length of the electrode. After TDR Base Time 105 passes, the TDR stores analog voltage detected 106 on the electrode in an analog timebase. Voltage 106 represents only a small portion of the entire reflected waveform 107. This analog voltage value is then converted to digital format by an analog-to-digital converter in TDR I/O 23, and then transmitted to logic and control section 11 for storage in output device, such as RAM 22. After a predetermined amount of time, such as 200 microseconds from the initiation of the first incident pulse, TDR I/O 23 generates second TDR pulse 108. The above process is repeated numerous (e.g. 256) times, except the time at which an analog voltage reading is stored in the analog timebase is incremented slightly with each cycle. As a result, RAM 22 has stored in it a raw TDR reading representing the reflected waveform.

After the TDR reading has been generated, logic and control section 11 sends a signal to pulse selector 26 causing the electrode connectors 14,15 and/or 16,17 to be electrically reconnected to the output section 13, and electrically disconnected from TDR I/O 23. The isolation of TDR I/O 23 from output section 13 by pulse selector 26 guards against any damage to the circuitry of TDR I/O 23 from stimulating pulses generated by output section 13. Thereafter, the generation of stimulating pulses may resume.

If the number of readings averaged parameter is greater than one, then the TDR reading process may be repeated, either immediately, if the time until the next stimulating pulse to be generated is sufficiently long, or else after the next stimulating pulse is generated. Taking multiple TDR readings and averaging them reduces any noise that may be inherent in a single reading. For averaged readings, instead of storing the each set of individual TDR waveform readings to the same RAM address, the digital values may be added to the previously stored values. After the total number of TDR readings specified by the "No. of Readings Averaged" parameter has been completed, the each sum may be divided by the number of readings comprising the sum to obtain a composite reading, namely the average. Alternatively, it is envisioned that merely the raw TDR readings may be transmitted to programmer 28 as described below, and programmer 28 perform the averaging of the readings.

It will be appreciated from the description of the foregoing embodiment that the time domain reflectormeter, i.e. the system for generating incident pulses and storing the reflected wave form, comprises a logic and control system as is already found in conventional pacemakers, as well as TDR I/O circuitry.

Figure 7:
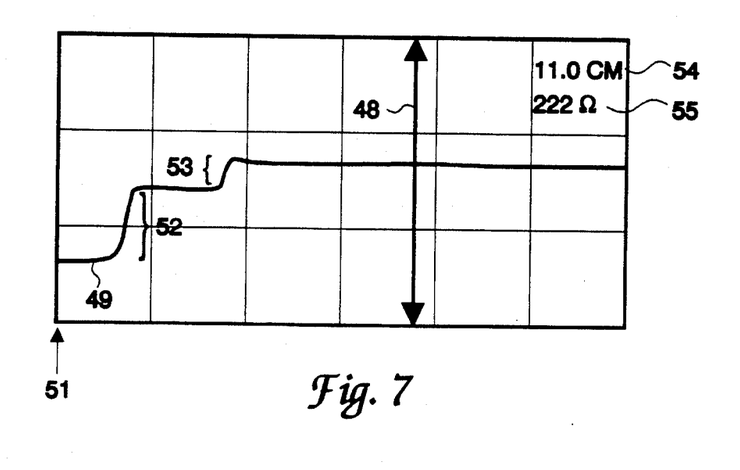
FIG. 7 is a representative graphically displayed TDR reading for an electrode have a short in it.

After the raw or composite TDR reading has been stored in RAM 22, logic and control section 11 transmits the stored raw or composite waveform through TDR reading output signal means, such as transceiver means comprised of telemetry transmitter 18 and antenna 20, to wand 27 of programmer 28. In addition, in the preferred embodiment, logic and control section 11, will also transmit to programmer 28, the stored sampling values used to take the TDR reading to programmer 28. This transmission assures that the correct parameter values may be displayed in association with the TDR reading. Programmer 28 then displays the received TDR reading in graphical form on a monitor (in graphical display window 411) or a printer, or both. Preferably, programmer 28 includes a Print button which when depressed, causes the displayed graph, and current configuration information to be printed. A representative TDR waveform for a working electrode is shown in FIG. 7. The horizontal axis represents the time, or sequential samples of the TDR reading, which can be directly converted into electrode distance if the $V_p$ of the electrode is known. As discussed above, this information may be supplied by the electrode manufacturer or manually programmed into the programmer. With a known $V_p$, the vertical gridlines, or divisions, represent a specific length from the TDR I/O output to the end of the electrode. The vertical axis of the waveform represents millirhos, which is directly convertible into impedance. Thus, a rise in the waveform represents increased resistance along the electrode, while a fall in the waveform represents a short circuit between the electrode and the pacemaker ground.

Accordingly, for the representative waveform shown in FIG. 7, waveform rise 52 represents an increase in resistance, which in this representative case, is attributable to the internal pacemaker wiring connection between the application specific integrated circuit on which pacemaker circuitry is connected and the wires connected to the pacing leads 14, 15, and 16, and 17. Second waveform rise 53 is attributable to the interconnection between electrode receptacle and the electrode plug. Thereafter, the waveform is flat, indicating a constant impedance throughout the length of the electrode, with no breaks or shorts.

Figure 5:
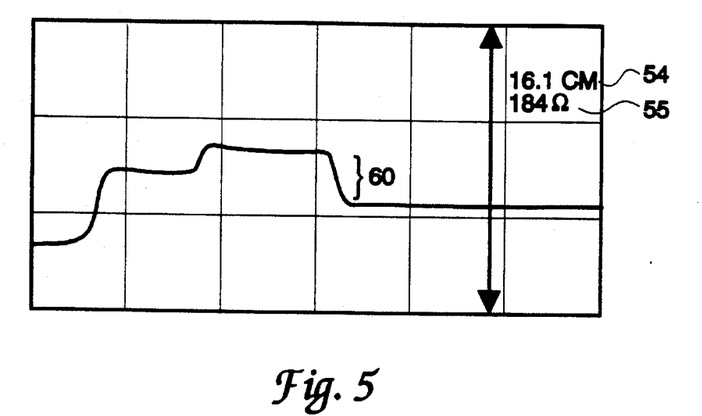
FIG. 5 is a representative graphically displayed baseline TDR reading for an electrode in good condition.

FIG. 5 shows a representative TDR reading in which the electrode has a partial short and is in need of replacement. Such a short may be caused, for example, by defective insulation between the leads of a bipolar electrode, or by the exterior insulation of the electrode becoming worn by, for example, excessive rubbing against a bone, pacemaker case or other structure. The short is evident by waveform fall 60, indicating the impedance of the electrode at that point has fallen.

At anytime while a TDR Reading is displayed, the physician may depress the cursor left 45 or cursor right 46 arrows below the display to cause graphical cursor 48 to move left or right. At the point where cursor 48 intersects waveform 49, the distance of the electrode circuit and impedance of the waveform are shown in displays 54 and 55. Thus, cursor 48 and displays 54 and 55 comprise means for superimposing a distance scale measurement corresponding to the length of the implanted electrode on the graphical display.

Figure 2:
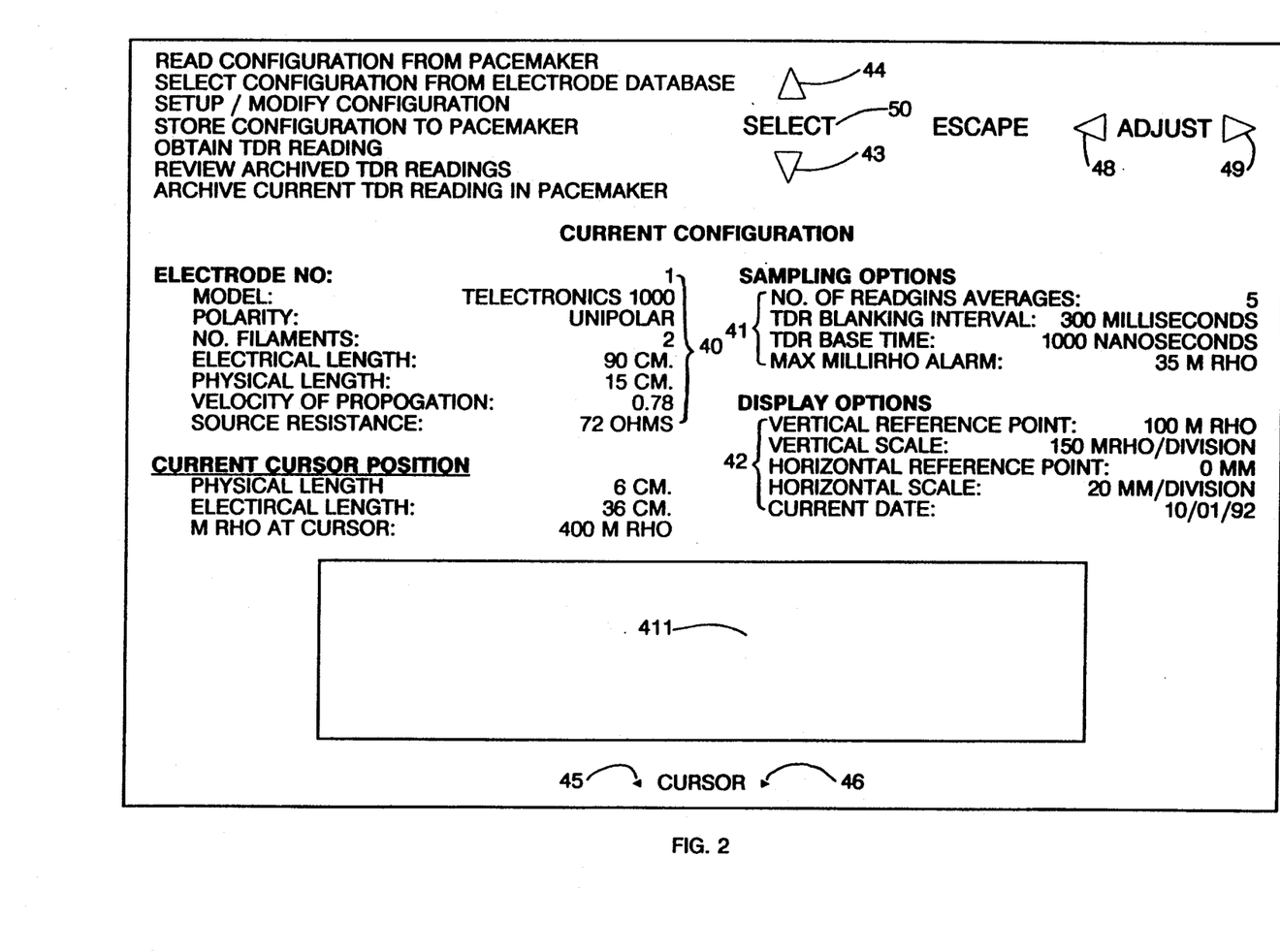
FIG. 2 a representative computer touch screen user interface for configuring and testing an implantable electrode according to the invention.

After the physician has obtained and displayed the composite TDR reading, the reading may be transmitted back to the pacemaker and stored in RAM 22, which comprises means for storing multiple TDR output signals. As shown in FIG. 2, this may be done by depressing the down arrow until the "Archive Current TDR Reading in Pacemaker" menu option is highlighted. The Select button is then depressed. This causes programmer 28 display a dialogue box on the screen in which the physician may type a short descriptive summary of the reading using a keyboard connected to programmer 28, such as "Pre-implant readings w/Technitronics 1000", and in which the physician may enter his or her name. After this option information has been entered, the Select button is again depressed, causing programmer 28 to transmit the TDR waveform, along with the Sampling Options, Display Options and textual information (including the date, which comprises a means for associating each stored output signal with a time reference indicating when the output signal is generated) through wand antenna 27 to antenna 20 of the pacemaker, accompanied by a command instructing the pacemaker logic and control 11 to store the information in RAM 22. This stored reading may be used as a baseline TDR reading against which future TDR readings may be compared to assist in evaluating electrode integrity. In one embodiment, RAM 22 has sufficient capacity to store up to 512 TDR readings and associated information. Logic and control 11 stores in RAM 22 an incremental counter indicating the total number of readings that have been stored in RAM 22 and the address of the next subsequent reading to be stored.

Assuming the initial TDR reading is acceptable, the physician may proceed with implantation of the pacemaker and electrode. Following implantation, but prior to closing the surgical incision in the patient, the physician may take a second TDR reading to ensure that no damage to the pacemaker or electrode occurred during implantation. Assuming the TDR reading is acceptable, the physician may close the incision.

Figure 3:
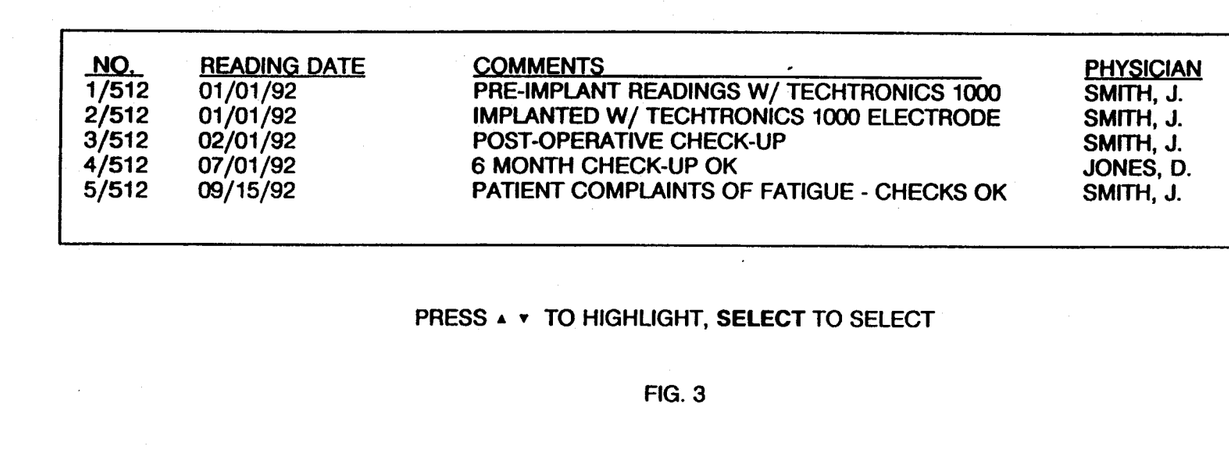
FIG. 3 is a representative computer screen list window displaying an index of previous TDR readings which have been stored in the device.

Following implantation, the patient can be expected to have numerous follow-up visits with the physician, during which the integrity of the implanted electrode may be evaluated. This may be done using the same programmer 28 described above. After the programmer is turned on, wand 27 is positioned over the patient's pacemaker, and the TDR option is selected, the screen shown in FIG. 2 may appear. The physician choose to first retrieve a copy of the archived TDR reading from when the electrode was first implanted. This may be done by using up 44 and down 43 arrows to highlight the "Review Archived TDR Readings" option, and depressing Select. This will cause programmer 28 to send a signal to the pacemaker instructing logic and control section 11 to transmit the archive number, date, comment and physician portions of each archived TDR reading to the programmer. An archived TDR display window, as shown in FIG. 3 is then displayed. Using up 44 and down 43 arrows, the physician may highlight an archived TDR reading, which will normally be the baseline reading or first reading archived after implantation. Depressing the Select portion of the screen causes programmer 28 close the widow and to command the pacemaker to transmit the selected archived TDR reading (including the electrode, sampling and display options) to the programmer, where they are displayed. The physician may then depress the up arrow to highlight the "Obtain TDR Reading" menu option, then press Select 50. This will cause a TDR reading to be generated as described above, and superimposed over the archived TDR reading.

By highlighting and adjusting the "Max Millirho Alarm" option, the physician may specify a millirho value (predetermined threshold) by which, if a TDR reading deviates in a relevant portion, an indicating output warning signal, such as a flashing light, buzzer, or "DEFECTIVE" screen display is generated. High and low limits from the electrode portion of the display waveform may be represented as horizontal lines on the graphical display. Specifically, minimum warning line 64 and maximum warning line 65 as shown in FIG. 67 define the boundaries in which the entire electrode portion of the waveform is expected to fall. If a waveform deviates from these limits, DEFECTIVE legend 66 may be displayed on the screen, preferably in a highly contrasting color and accompanied by an audible alarm.

Figure 6:
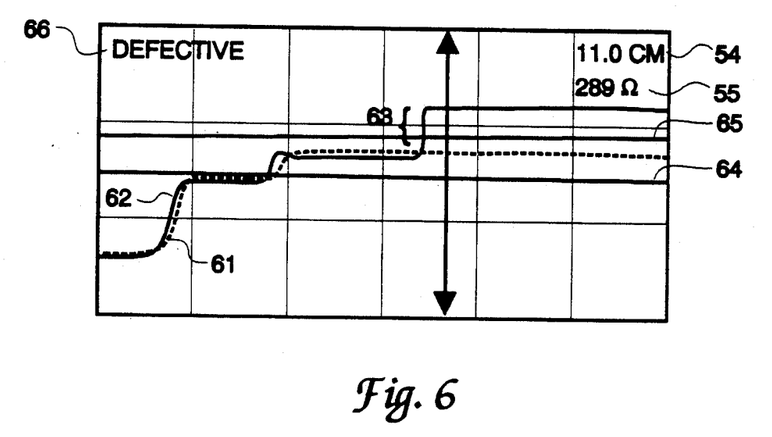
FIG. 6 is a representative graphically displayed baseline TDR reading having superimposed over it a more recent TDR reading for the same electrode showing that a break has occurred in the electrode and that the electrode is now defective.

FIG. 6 shows a representative superimposed TDR reading, in which archived reading 61 shows an electrode in good condition, while current reading 62 shows that the electrode has broken. Specifically, reading 62 includes waveform rise 63, indicating that the impedance of the electrode has risen. This may be caused by, for example, a filament becoming cracked or completely severed. Because current reading 62 exceeds maximum alarm level 65, DEFECTIVE legend 66 is displayed on the screen, alerting the physician that the electrode may be defective.

The Current Configuration parameters 40, 41 and 42 shown in FIG. 2, as mentioned above, may be adjusted. With regard to Display Options 42, these parameters effect how a particular TDR reading is displayed on the screen. In particular, different electrodes from different manufacturers and for different purposes will generate TDR readings have different impedance baselines and lengths. In order to scale a TDR reading on the graphical display, the Vertical and Horizontal reference points and scales may be adjusted. These values will also be stored along with an archived TDR reading so that when the reading is retrieved, it will be initially displayed using the same viewing parameters as when it was stored.

It will be appreciated to those of skill in the art that may changes could be made in the foregoing representative embodiment without departing from the spirit and scope of the invention. For example, the present invention may be used with virtually any type of medical electrode, such as ventricular, rate sensing, morphology, high voltage, mapping, sensor, temporary, ablation and angio/artheretomy electrodes. The invention may also be used in connection with wires used in connection with devices such as insulin pumps, and such wires are within the scope of the term "electrode" as used herein and in the claims. In addition, in instances where a tube or stint is implanted in a patient, a tube configured with an embedded electrical conductor running the length of the tube and connectable to a TDR, and which will break if the tube breaks, is also included within the definition of an electrode as used herein. Electrodes as used herein also include electrical conductors that are external to a patient used to send or receive electrical signals, such as, for example, ECG electrodes, or external pacemaker or defibrillator leads.

It will also be appreciated that although the in the embodiment described above a TDR reading is output through RAM and an RF antenna, other transceiver or output means are within the spirit and scope of the invention. For example, virtually any other electromagnetic wave communication means may be used, at any desired frequency, including optical frequencies, or wire leads may be used to transmit a TDR reading. Moreover, the TDR reading described above is obtained by generating multiple incident pulses and storing a small portion of each reflected pulse. It is contemplated that with the development of faster electronic and CPU circuitry, that a TDR reading may possibly be generated by storing the reflected wave from a single incident pulse, and such systems included within the definition of a TDR. It will also be appreciated that in the embodiment described above, a user-selected number of multiple raw TDR readings may be averaged to produce a composite reading to eliminate noise associated with individual readings. The averaging function could easily be transferred from the internal implantable device to external programmer 28. Moreover, other manipulations of raw TDR readings, such as by averaging multiple readings, would not necessarily alter their definition as being a TDR reading. Other functions contemplated to be performed by the pacemaker could also be performed by external programmer 28. For example, the storage of TDR readings could be performed on external programmer 28, and optionally, may be indexed by a unique key, such as patient social security number or pacemaker serial number, to distinguish between stored readings from different patients. Also, graphical display of programmer 28 may include means for displaying the amplitude differential between the incident pulse and a selected portion of a TDR reading.

Figure 9:
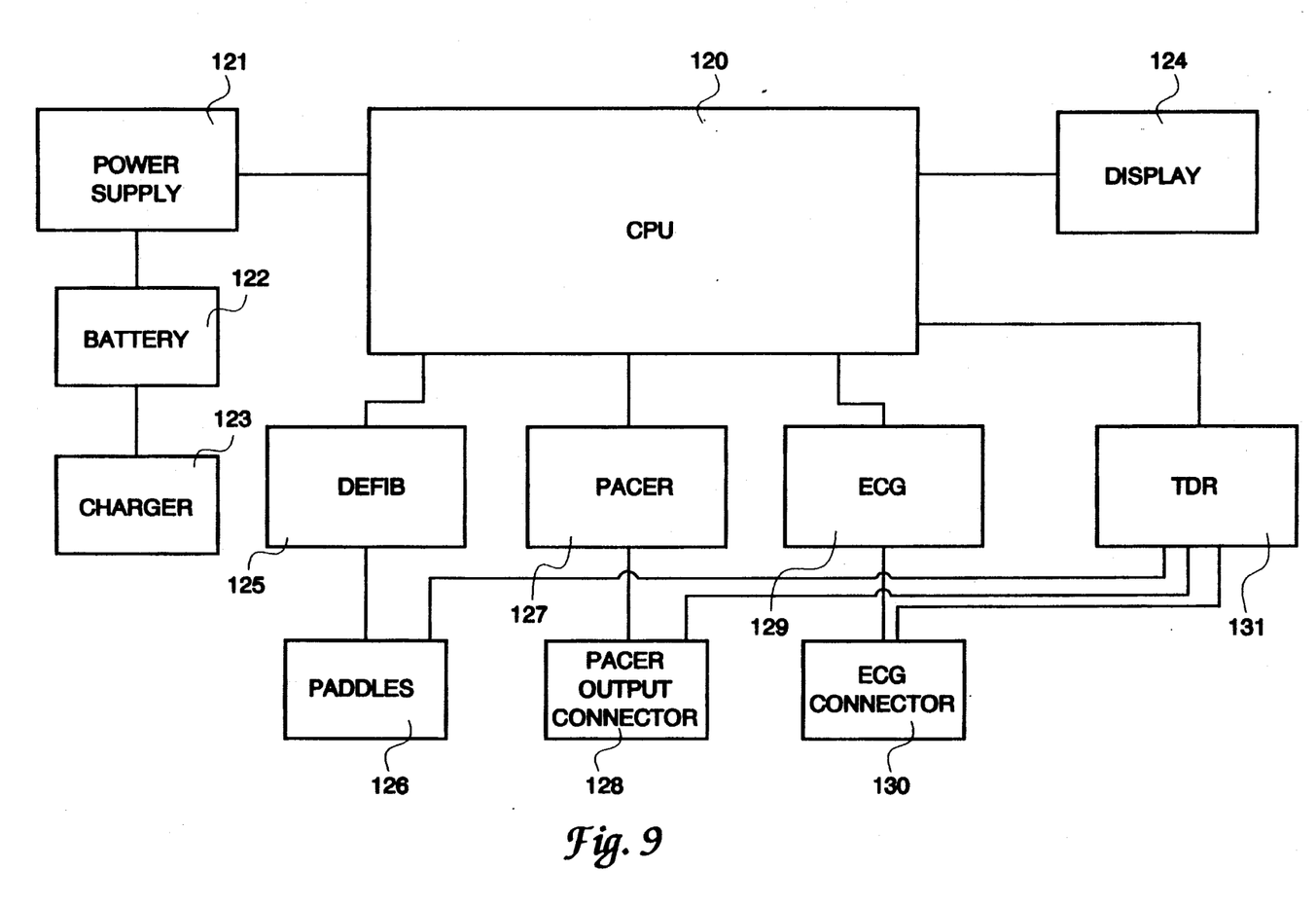
FIG. 9 shows a block representative diagram of one embodiment of the device of the present invention when used in connection with a portable, external defibrillator/pacemaker.

Referring now to FIG. 9, there is shown a representative block diagram of one embodiment of the device of the present invention when used in connection with a portable, external defibrillator/pacemaker. The defibrillator/pacemaker includes a central processing unit (CPU) 120 (which includes appropriate memory and software to carry out the functions described herein), power supply 121, battery 122, charging circuitry 123 and display 124. The device is powered by battery 122 and may be recharged by charger circuitry 123. Display 124 may comprise a computer screen, LCD display, plotter, or other such similar device. In this embodiment, three primary functions are provided by the defibrillator/pacemaker. First, the device may serve as a defibrillator through defibrillator circuitry 125, which is responsible for the delivery of energy to defibrillator paddles connector 126 connected to defibrillator circuitry 125. The second function of the defibrillator/pacemaker is as a pacemaker. Pacing circuitry 127, connected to pacer output connector 128, delivers pulses to electrodes (see FIG. 11) connected to pacer output connector 128. Third, the defibrillator/pacemaker includes the capability to monitor the ECG signal of a patient through ECG circuitry 129 connected to ECG connector 130. In addition to these conventional functions of the defibrillator/pacemaker, the device also includes TDR circuitry 131 connected to CPU 120 and to defibrillator paddles connector 126, pacer output connector 128 and ECG connector 130.

As discussed in detail for the embodiment of the invention illustrated in FIGS. 1-8, TDR circuitry 131 includes the circuitry necessary to generate a TDR pulse and to detect the resulting voltage. Such a pulse may be caused to travel to individual defibrillator paddles connector 126 and the paddles connected thereto, or through an electrode connected to pacer output connector 128 or ECG connector 130. Circuitry for time domain reflectometers is well known and, in isolation, does not form the present invention.

Figure 10:
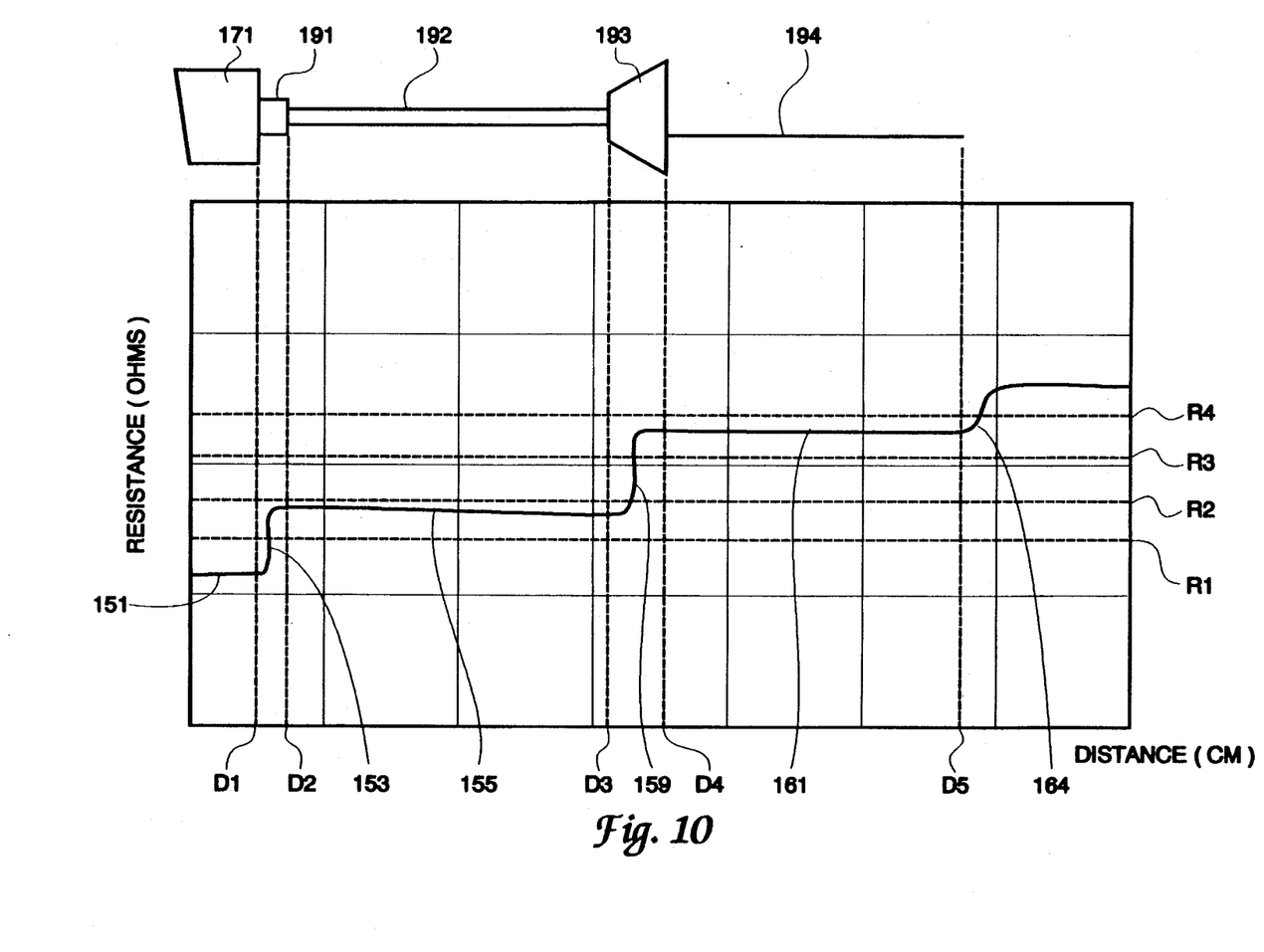
FIG. 10 is a representative graphically displayed baseline TDR reading and a corresponding representative diagram a patient cable connected to an electrode, both of which are in good condition.

FIG. 10 is a representative graphically displayed baseline TDR reading and a corresponding representative diagram of a patient cable connected to an electrode tip, both of which are in good condition. Such a configuration may be such as connected to pacer output connector 128 (see FIG. 9) wherein a patient cable is connected to the pacer output connector and an electrode tip is connected to the patient cable. In the display of resistance versus distance over which the TDR pulse travels, the distance from the origin of the graph to distance D1 represents the internal circuitry of medical device 171 and the resistance of internal circuitry 151 is shown to be substantially constant. First connector 191, connecting patient cable 192 to device 171 is represented by first connector resistance curve 153 between distances D1 and D2. A rise in resistance occurs over the distance comprising first connector 191. From the beginning of patient cable 192 to the end of the patient cable 192, represented by distance D2 to D3, patient cable resistance 155 is shown. Patient cable resistance 155 is substantially constant and is expected to be between minimum patient cable resistance value R1 and maximum patient cable resistance value R2. Should patient cable resistance 155 achieve a value outside of predetermined thresholds, namely the minimum and maximum values R1 and R2, respectively, it is known that there is a short, break or other discontinuity in patient cable 192. Second connector 193 connects patient cable 192 to electrode tip 194 and is represented by the distance D3 to D4. In the range between distance D3 and distance D4, second connector resistance 159 rises as indicated. From the beginning of the electrode 194 to the end of the electrode tip 194, represented by distance D4 to D5, electrode resistance 161 is substantially constant and should reside within the predefined threshold range between minimum electrode resistance value R3 to maximum electrode resistance value R4. At the termination of electrode 194 at a distance D5, the value of resistance rises as shown if electrode 194 is not connected to a patient, i.e., if there is an open circuit. In one embodiment, the upper and lower resistance thresholds are plus or minus ten percent (10%) of the expected resistance at any distance along the completed circuit.

It will be appreciated by those of skill in the art that much of the analysis discussed herein with regard to the embodiment of the invention illustrated in FIGS. 1-8 may be used to determine whether patient cable 192 and electrode 194 or connectors 191 and 193 are within desired resistance range or, more specifically, whether there is a problem of significance with patient cable 192, electrode tip 194 or connectors 191 and 193. However, it is desirable to provide a simplistic method of displaying the information to a technician or a physician. Remembering that time is of the essence in the use of the external devices, the display should be such that a problem is quickly discernable by the operator.

Figure 11:
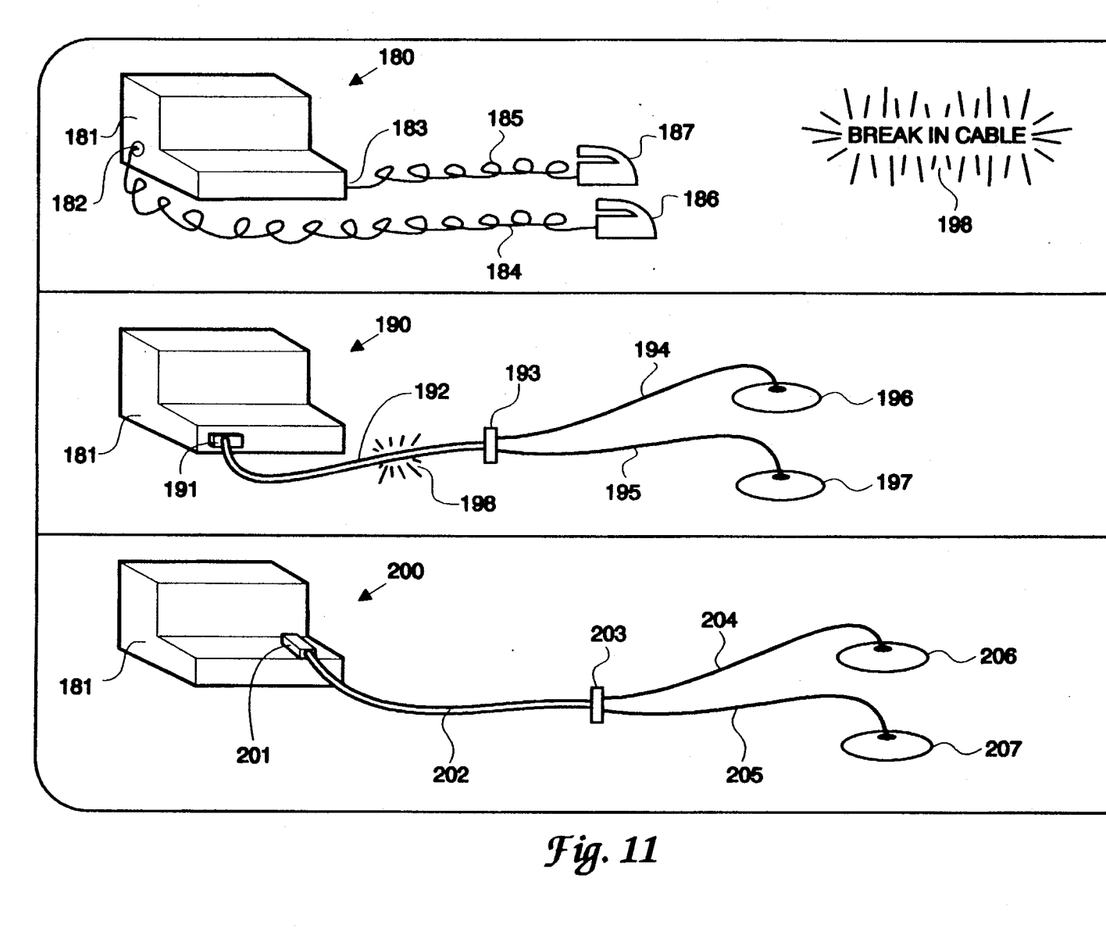
FIG. 11 is a representative computer screen of a defibrillator/pacemaker in which the patient cable is defective.

Referring now to FIG. 11, there is shown a representative computer screen of an external, portable, temporary defibrillator/pacemaker in which the patient cable is defective. The display is divided into three sections. First display section 180 illustrates defibrillator/pacemaker 181 having first and second defibrillator cables 184, 185 connected to first and second to paddles 186, 187 respectively and also connected at first and second defibrillator connectors 182, 183 of defibrillator/pacemaker 181. Second graphical section 190 illustrates the configuration of defibrillator/pacemaker 181 when used in the pacing mode. Patient cable 192 is connected to defibrillator/pacemaker 181 at cable connector 191 (which may be equivalent to pacer output connector 128 shown in FIG. 9). At the other end of patient cable 192 is connector 193 to which first and second pacing electrodes 194, 195 are connected. Thereafter, electrodes 194, 195 are connected to first and second pacing electrode pads 196, 197, respectively, which are placed on the patient. It should be noted that pacing electrodes 194, 195 need not be connected to pacing electrodes pads 196, 197 for integrity testing of electrodes 194, 195 to be performed.

Third graphical display section 200 shows defibrillator/pacemaker 181 when used is connection with first and second monitoring electrodes 204, 205 for the purpose of monitoring ECG signals. In the ECG monitoring configuration, patient cable 202 is connected to defibrillator/pacemaker 181 by connector 201 and to monitoring electrodes 204, 205 at its other end. As discussed above, monitoring electrodes 204, 205 may be connected to monitoring electrode pads 206, 207, respectively, which are then in turn placed on the patient. It will be appreciated by those of skill in the art that the display actions are dependent on the device and connectors employed. For example, third graphical display function 200 may not be necessary should the ECG monitoring function operate through the same connectors and cables/wires as are used for the pacing function of defibrillator/pacemaker 181.

In FIG. 11, second graphical display section 190 is highlighted indicating defibrillator/pacemaker 181 is in its pacing configuration. Along patient cable 192 is a marked or highlighted trouble area 198. Also at the top right of the display is message 199, BREAK IN CABLE, which is also highlighted or marked. This simple display, which may be accompanied by an audible alarm, immediately informs the physician or technician that there is a discontinuity of significance in patient cable 192 which requires replacement of patient cable 192 for the proper operation of defibrillator/pacemaker 181.

It will be appreciated by those of skill in the art that there may be discontinuities or breaks in either first electrode 194 or second electrode 195 in this configuration. One of the advantages of the use of TDR technology is that more than one problem can be identified and displayed to the physician or technician. Moreover, the system may be easily tested by, for example, intentionally unplugging an electrode from the system and determining whether a BREAK IN CABLE message is displayed.

It will also be appreciated by those with skill in the art that TDR technology may be used in connection with a variety of types of wires, cables, or electrodes extending from such a medical device. The technology need not be limited to a particular type of cabling, nor should the requirement of the device to use a successive connections of various cable types preclude the use of the technology to determine defects in the attached cabling. Thus, the term "electrode" as used in the claims may encompass defibrillator cables, patient cables, electrodes or other wires, or to any combination thereof, extending from such a medical device. Also, the term "medical device" as used in the claims may encompass any electrical device used in the medical profession wherein an "electrode," as defined herein, is connected to the device.

It will be further appreciated that the TDR technology is not limited to a single wire connected to a medical device. Rather, the technology may be used for any and all wires, cables, sensors or pads extending from the medical device. In this manner, the technician may check the system prior to its use to insure that the components are all operational. Accordingly, as used herein and in the claims, the term "electrode" includes all of the components used to carry an electrical signal from the instrumentation to the patient and back, even where this consists of discrete pieces electrically connected together.

It will further be appreciated that the system of the present invention can not only test for electrode integrity prior to use, but during operation of the medical device. Such a feature is desirable because with the frantic pace at which medical technicians operate during a medical emergency, it is possible for electrical cables to become inadvertently pulled and thereby reduce the integrity of the electrical connections between them. Thus, in one embodiment of the invention, CPU 120 is programmed through conventional software to monitor a patients heartbeat through ECG connector 130. As the heartbeat occurs on a periodic basis, CPU 120 can detect point in time when it is between heartbeats, and therefore little or no electrical activity on ECG electrodes. At such a point, CPU causes a signal to be transmitted to ECG 129 to cause its electrical connection to ECG connectors to be disabled, and a signal to be transmitted to TDR 131, to cause its output to be connected to ECG connector 130. A TDR reading is then taken by TDR 131. CPU 120 then transmits a signal to TDR 131 causing it to electrically disconnect from ECG connector 130, and to ECG 129, causing it to reconnect to ECG connector 130. The combination of these components act as an anticoincidence detector to eliminate the possibility of a TDR reading being taken at the same time a signal is transmitted on the ECG electrodes to monitor the heartbeat. Due to the short time period needed to take a TDR reading, there is no appreciable interruption in ECG readings. However, the TDR reading can be stored in memory and compared to a reference TDR signal for the ECG connectors, as described above. If the comparison indicates that a break or short in a ECG electrode has occurred, a graphical display showing the location of the break and an audible alarm are generated. It will also be appreciated that the above procedure can also be employed for the defibrillator output and pacing outputs, so the integrity of the entire system may be tested.

As it is contemplated that the TDR circuitry may be reduced to a small and inexpensive application specific integrated circuit, it is also within the spirit and scope of the invention that separate TDR's be provided for each electrode circuit, instead of providing a single TDR with switch means which may be used to connect the TDR to different electrodes. It is also contemplated that different types of TDR readings may be taken for different types of electrodes. For example, for longer electrodes, it may be desirable to take a TDR reading consisting of 1,024 time divisions instead of 256 divisions. In addition, the gain and resolution at which TDR reading may be graphically displayed may very depending on the electrode being tested. It is contemplated that such parameters may be separately stored for each electrode in a system, and automatically recalled and used to take a particular TDR reading.

It will further be appreciated that the system of the present invention may include an integral graphical printer and a test mode switch. When the test mode switch is activated, CPU 120 automatically cycles through each electrode in the system and conducts an integrity test, the results of which may be printed out with a date and time stamp. Such a system allows its integrity to be checked on a routine basis and before a medical emergency. In addition, the printout can provide written documentation that the system was checked at the designated time.

What is claimed is:

1. An electrical medical device comprising:
   means for receiving a first electrode,
   means for transmitting a first electrical signal to the electrode receiving means,
   time domain reflectometer means operatively connected to the electrode receiving means such that at a time domain reflectometer pulse may be transmitted to the electrode receiving means, the time domain reflectometer means comprising output signal means, and
   anti-coincidence means preventing a time domain reflectometer pulse from being transmitted to the electrode receiving means when a first electrical signal is being transmitted to the electrode receiving means.

2. The device of claim 1 wherein the device comprises a pacemaker.

3. The device of claim 1 wherein the device comprises a defibrillator.

4. The device of claim 1 wherein the output signal of the means comprises a TDR reading from the time domain reflectometer.

5. The device of claim 1, wherein the output signal means comprises means for graphically displaying a TDR output signal.

6. The device of claim 1, further comprising:
   means for storing a reference TDR signal representative of a TDR signal from a working electrode connected to the electrode receiving means,
   means for comparing a TDR output signal to a stored reference TDR signal,
   means for indicating whether the TDR output signal varies from the stored reference TDR signal by a predefined threshold.

7. The device of claim 6 wherein the means for indicating comprises a graphical display of an electrode.

8. The device of claim 7 further comprising means for graphically displaying the relative point on the graphically displayed electrode where the TDR output signals varies from the stored reference TDR signal by the predefined threshold.

9. The device of claim 1, further comprising means for receiving at least one additional electrode, the time domain reflectometer means being operatively connected to the at least one additional electrode receiving means such that at a time domain reflectometer pulse may be transmitted to the at least one additional electrode receiving means.

10. The device of claim 9, further comprising at least one ECG reading electrode connected to at least one of the electrode receiving means.

11. The device of claim 9, further comprising means for automatically causing a TDR reading to be taken on each electrode receiving means.

12. A method of analyzing the integrity of a first medical electrode for transmitting an electrical signal, comprising the steps of:
   providing means for transmitting an electrical signal on the first electrode, the transmitting means being capable of being selectively enabled and disabled,
   providing a time domain reflectometer (TDR) operatively connected to the first electrode,
   disabling the transmission of electrical signals on the first electrode,
   generating a first TDR reading from the first electrode and outputting the TDR reading,
   reenabling the transmission of electrical signals on the first electrode.

13. The method of claim 12 wherein the means for transmitting comprises a means for transmitting pacemaker pulses.

14. The method of claim 12 wherein the means for transmitting comprises a means for transmitting a defibrillator pulse.

15. The method of claim 12 wherein the means for transmitting comprises a means for transmitting an ECG reading signal.

16. The method of claim 12, wherein the disabling of the transmission of electrical signals on the first electrode occurs based on the timing of heartbeats of a patient to whom the electrode is connected.

17. The method of claim 12, further comprising the steps of:

storing a reference TDR signal representative of a TDR signal from a working electrode connected to the electrode receiving means, comparing the outputted TDR signal to the stored reference TDR signal, and indicating whether the outputted TDR signal varies from the stored reference TDR signal by a predefined threshold.

18. The method of claim 17 wherein the indicating step includes graphically displaying an electrode.

19. The method of claim 17 wherein the indicating step further includes, if the outputted TDR signal varies from the stored reference TDR signal by a predefined threshold, graphically displaying the relative point on the graphically displayed electrode where the TDR output signals varies from the stored reference TDR signal by the predefined threshold.

20. The method of claim 12, further comprising the steps of:

providing at least one second medical electrode, and providing means for operatively connecting the TDR to the at least one second medical electrode such that a time domain reflectometer pulse may be transmitted thereto, and providing means for selecting which of the electrodes the TDR may be operatively connected to.

21. The method of claim 20, wherein the means for selecting comprises automatic means for automatically causing a TDR reading to be taken on each medical electrode.

22. The method of claim 12, further comprising the step of graphically displaying the outputted TDR reading.

23. The method of claim 12, further comprising the steps of:

selecting a portion of the generated TDR reading, and graphically displaying the selected portion of the TDR reading.

* * * * *